(12) United States Patent
Harbury et al.

(10) Patent No.: US 7,479,472 B1
(45) Date of Patent: Jan. 20, 2009

(54) DNA-TEMPLATED COMBINATORIAL LIBRARY CHEMISTRY

(75) Inventors: Pehr B. Harbury, San Francisco, CA (US); David R. Halpin, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/421,422

(22) Filed: Oct. 19, 1999

Related U.S. Application Data

(60) Provisional application No. 60/104,744, filed on Oct. 19, 1998.

(51) Int. Cl.
| | |
|---|---|
| *C40B 50/14* | (2006.01) |
| *C12Q 1/68* | (2006.01) |
| *C12N 15/00* | (2006.01) |
| *C07H 19/00* | (2006.01) |

(52) U.S. Cl. .................... 506/30; 435/6; 435/320.1; 536/22.1

(58) Field of Classification Search ............... 435/91.2, 435/6, 320.1; 536/25.3, 22.1; 436/518; 506/30
See application file for complete search history.

(56) References Cited

U.S. PATENT DOCUMENTS

| | | | | | |
|---|---|---|---|---|---|
| 5,573,905 | A | * | 11/1996 | Lerner et al. | 435/6 |
| 5,604,097 | A | * | 2/1997 | Brenner | 435/6 |
| 5,635,400 | A | * | 6/1997 | Brenner | 435/320.1 |
| 5,668,266 | A | * | 9/1997 | Ruth | 536/25.3 |
| 5,723,320 | A | * | 3/1998 | Dehlinger | 435/91.1 |
| 5,723,598 | A | * | 3/1998 | Lerner et al. | 536/25.3 |
| 5,763,263 | A | | 6/1998 | Dehlinger | |
| 5,811,238 | A | | 9/1998 | Stemmer et al. | |
| 5,962,228 | A | * | 10/1999 | Brenner | 435/6 |
| 6,027,890 | A | * | 2/2000 | Ness | 435/6 |
| 6,607,878 | B2 | * | 8/2003 | Sorge | 435/6 |

FOREIGN PATENT DOCUMENTS

| | | |
|---|---|---|
| WO | WO9321340 | * 10/1993 |
| WO | WO 97/35198 | 9/1997 |

OTHER PUBLICATIONS

Brenner and Lerner. Encoded combinatorial chemistry. PNAS 89:5381-5383. 1992.*
Terret. N.K. "Combinatorial Chemistry" (1998) Oxford University Press, pp. 4, 8, 26, 64, 97, and 102.*
Brenner et al., "Encoded combinatorial chemistry", 1992, Proc. Natl. Acad. Sci., 89(15):5381-5383.*
David R. Liu, "Translating DNA into Synthetic Molecules", Jul. 2004, PLoS Biology, vol. 2, Issue 7, pp. 905-906.*
Halpin et al., "DNA Display III. Solid-Phase Organic Synthesis on Unprotected DNA", Jul. 2004, PLoS Biology, vol. 2, Issue 7, pp. 1031-1038.*
Greene et al., Protective Groups in Organic Synthesis. 3rd ed. NY. Apr. 1999; p.v, pp. 1-5, pp. 502-503 only.*
Brenner, S., and Lerner, R.A., "Encoded combinatorial chemistry" *Proc. Natl. Acad. Sci.* USA 89:5381-5383 (1992).
Crameri, A., et al., "DNA shuffling of a family of genes from diverse species accelerates directed evolution" *Nature* 391:288-291 (1998).
Czarnik, A.W., "Encoding strategies in combinatorial chemistry" *Proc. Natl. Acad. Sci.* USA 94:12738-12739 (1997).
Ellman, J.A., and Gallop, M.A., "Combinatorial chemistry" *Curr Opin Chem Biol* 2:317-319 (1998).
Stemmer, W.P.C., et al., "Single-step assembly of a gene and entire plasmid from large numbers of oligodeoxyribonucleotides" *Gene* 164:49-53 (1995).

* cited by examiner

*Primary Examiner*—Jd Schultz
*Assistant Examiner*—Sue Liu
(74) *Attorney, Agent, or Firm*—Carol L. Francis; Bozicevic, Field and Francis LLP

(57) ABSTRACT

The present invention describes templated combinatorial chemical libraries comprised of a plurality of bifunctional molecules having both a chemical compound and a nucleic acid tag that defines the structure of the chemical compound and directs its synthesis. Also described are methods for producing, enriching and in vitro evolution of the bifunctional molecules of such libraries based on the nucleic acid tags and methods for selecting for library compounds having a desired activity.

25 Claims, 2 Drawing Sheets

DNA-TEMPLATED COMBINATORIAL LIBRARY CHEMISTRY

This application is based on U.S. Provisional Application Ser. No. 60/104,744 filed on Oct. 19, 1998, which is incorporated herein by reference.

FIELD OF THE INVENTION

The present invention relates to compositions and methods for synthesizing a DNA-templated combinatorial chemistry library of compounds, the selection of compounds with a desired activity and genetic recombination and in vitro evolution of selected compounds. The invention further includes the nucleic acid tags which direct the synthesis of the compound library, and the library of compounds produced by the methods of the invention.

BACKGROUND OF THE INVENTION

There is widespread interest in efficient synthesis and screening of large numbers of compounds to identify candidate compounds with a given desired activity. [Ellman, J A and Gallop, M A, Curr Opin Chem Biol 2:317-319 (1998)].

Combinatorial libraries of random-sequence oligonucleotides, polypeptides, synthetic oligomers and small organic molecules have been described and their utility in identifying active compounds or as a starting point for developing related molecules with more desirable properties has been proposed (Ellman, J A and Gallop, M A, 1998).

One method for formation of combinatorial libraries involves preparation of high density position-addressable oligomer arrays on a planar substrate. In this method, a substrate having photoprotective groups is irradiated, using photolithographic mask techniques, in selected regions only, to deprotect surface active groups in those selected regions. The entire surface is then treated with a solution of a selected subunit, which itself has a photoprotected group, to react this subunit with the surface groups in the photodeprotected regions. This process is repeated to (i) add a selected subunit at each region of the surface, and (ii) build up different-sequence oligomers at known, addressable regions of the surface. [See, e.g., Fodor, S. P., et al., Science 251:767-773 (1991) and U.S. Pat. No. 5,143,854 (1992)].

This method has the advantage that reaction sites do not have to be physically separated during subunit addition, and therefore massive parallel subunit addition is possible by applying subunit-addition reagents over the entire surface of the array. Greater site density is therefore feasible than in systems where physical separation of reagents is required from one reaction site to another, and where individual reagents are spotted or deposited in defined array regions.

A related approach wherein the library is produced in capillary tubes has also been described wherein a method for producing, high-density, position-addressable combinatorial library of different-sequence oligomer or different-substituent small molecule compounds. The disclosed invention includes massive parallel synthesis of subunits and known, addressable library positions in a dense array of capillary tubes, and the screening of individual library compounds in either solution phase or solid phase. [U.S. Pat. Nos. 5,723,3204 (1998), 5,759,779 (1998), and 5,763,263 (1998)].

In a related approach, a traditional split-and-recombine strategy for synthesis of combinatorial libraries has been described. [Chen, et al., Methods in Enzymology 267:211-9 (1996); Ellman and Gallop, (1998)]. In one application of this approach, beads containing successive precursors to the target compounds that form the library may be alternately mixed and separated, with one of a selected number of reagents being added to each group of separated beads at each step [Furka, A., et al., Int. J. Pept. Protein Res. 37:487-493 (1991); Chen, C. et al., J. Am. Chem. Soc. 116:2661-2662 (1994); Pham, E. K. et al., PCT Intl. App. Pub. No. WO 9513538 (May/1995); Dillard, L. W. et al., PCT Intl. App. Pub. No. WO 9408051 (April/1994)]. An advantage of this method is that each bead contains only one chemical species, allowing the beads themselves to be used for screening. However, the identity of the species on each bead must be independently determined. Although several methods have been reported for tagging the support beads with molecules more readily analyzable than the library members themselves [e.g., Nestler, H. P. et al., J. Org. Chem. 59:4723-4724 (1994); Felder, E. et al., PCT Intl. Appn. Pubn. No. WO 9516209 (June/1995); Dillard, et al., 1994], the need for separate identification of each species nonetheless limits the usefulness of this approach for the preparation of very large libraries.

Replacements for the conventional bead support for combinatorial synthesis have also been described, e.g., use of linear homogeneous polymers such as polyethylene glycol chains [Janda and Han, Methods in Enzymol 267:234-247 (1996); Han et al. Proc. Nat Acad. Sci. USA 92(14):6419-6423 (1996)], and fluorinated hydrocarbon chains [Studer et al., Science 275(5301):823-826 (1997)]. On the basis of their solubility properties, these polymers have been exploited as selective "handles" to extract split-and-recombine library members from complex reaction mixtures. The various polymer supports useful in combinatorial library formation of same molecules have been recently reviewed. [Labadie, Curr Opin Chem Biol 2:346-352 (1998)].

Another general approach involves the synthesis of a combinatorial library as a physically segregated array of compounds [Geysen, H. M., et al., Proc. Natl. Acad. Sci. USA 81:39984002 (1984); Southern, E., EP Patent No. 373,203 (1994); Southern, E. et al., Genomics 13:1008-1017 (1992); Bunin, B. A., et al., J. Am. Chem. Soc. 114:10997-10998 (1992); Bunin, B. A., et al., Proc. Natl. Acad Sci. USA 91(11): 4708 (1994); DeWitt, S. H. et al., Proc. Natl. Acad. Sci. USA 90:6909-6913 (1993)]. Libraries of compounds have been synthesized on functionalized resins either coated on (Geysen, et al, 1984, 1985; Bunin, et al., 1992, 1994) or contained within (DeWitt, et al., 1993) arrays of pins, with reactions carried out in separate chambers. Southern (1994) used arrays of spots laid down on a substrate such as glass by a pen plotter.

A key advantage of this approach is that the chemical identity of each library element on the array is associated with an addressable position on the array. However, in this method, as well as the split-mix method, preparation of very large libraries would require an inconvenient number of manipulations and/or a large array of separate reaction vessels or sites.

In cases where the compounds may be screened for biological activity while still attached to the substrate, this method also allows for massive and rapid screening, by binding a reporter-labeled target to the surface and determining the positions of bound target. Surface arrays of this type may be used both for combinatorial library screening (Fodor, S. P. A., et al., PCT Application WO 95/00530, published January, 1995; Geysen, et al., 1984, 1985) or for various types of oligonucleotide analysis, such as sequencing by hybridization (Drmanac, et al., 1993; Southern, 1994).

In a further approach, two alternating parallel combinatorial syntheses are performed such that a genetic tag is chemically linked to the chemical structure being synthesized. [See, e.g, Brenner and Lerner, Proc. Nat Acad. Sci. USA 89(12): 5381-5383 (1992); Lerner et al., U.S. Pat. No. 5,723,598

(1998)] In this method, the addition of a chemical unit is followed by the addition of an oligonucleotide sequence, which functions as an identifier for the structure of the chemical unit. A library is built up by the repeating the process after pooling and division of the reaction products obtained at each step.

One limitation in the early methods of combinatorial library formation is that large-library planar arrays are necessarily limited in the amount (number of molecules) of each library species, since the planar region available to each species is quite small, e.g., on the order of $10^2$-$10^3$ $\mu m^2$. As a consequence, the ability to detect binding species on the array may be limited. Further, it is not feasible to carry out solution-phase screening on a planar array, because of the difficulty of physically separating different array regions carrying different library members.

It would thus be desirable to provide a method for preparing a large combinatorial library of compounds which has the advantages of (i) massive parallel synthesis of subunits and known, addressable library positions, (ii) adaptable to virtually any oligomer or small-molecule chemistry, (iii) a relatively large area for synthesis of each library member, (iv) capable of being screened either as a mixture or as individual library compounds in either solution phase or solid phase, and (v) capable of amplifying and modifying selected library compounds.

SUMMARY OF THE INVENTION

The present invention provides methods and compositions for iterative synthesis and screening of a plurality of compounds wherein a nucleic acid tag directs and encodes the synthesis of the compound to which it is covalently attached, and the tag is a DNA molecule which can be amplified biochemically.

The methods of the present invention provide for synthesis of a plurality of compounds in a combinatorial library by way of a split and combine synthesis strategy, wherein synthesis is directed by the nucleic acid tag. The library may be provided in solution or attached to a solid support.

The nucleic acid tags useful in the methods of the present invention comprise nucleic acid sequences having a plurality of different first hybridization sequences, a mixture of different second hybridization sequences, and a chemical reaction site.

The present invention further provides a library of nucleic acid tags, also termed nucleic acid supports for use in directing the synthesis of a plurality of compounds wherein each tag has a first segment having a selected one of a plurality of different first hybridization sequences, a mixture of different second hybridization sequences, and a chemical reaction site; and a second segment having a selected one of a plurality of different second hybridization sequences and a mixture of different first hybridization sequences.

The methods of the present invention provide subsets of nucleic acid tags generated by base-specific duplex formation between each different first hybridization sequence and a complementary oligonucleotides or oligonucleotide analogs. The chemical reaction sites in each of the subsets are reacted with a selected reagent to form a reagent-specific compound intermediate.

The methods of the present invention further provide that the steps of formation of subsets of nucleic acid sequences by base-specific duplex formation be repeated and a chemical subunit added to the chemical reaction site or last added chemical subunit within each subset until synthesis of the plurality of compounds is complete.

In an exemplary aspect of the present invention, the nucleic acid tags include alternating spacer and hybridization sequences, wherein the spacer sequences are the same for all subsets of nucleic acid sequences and the hybridization sequences are different for each subset of nucleic acid sequences.

In a related aspect, the spacer sequence portion of each nucleic acid sequence has a restriction enzyme site which is unique to a given spacer sequence.

The methods of the present invention provide for the synthesis of small molecules with different chemical sequences, catalysts useful for the synthesis of complex molecules from simple substrates, inorganic compounds with useful properties as materials, non-ribosomally produced polypeptides, peptoids, polyketide-based natural products or subunit oligomers, e.g., polypeptides, polynucleotides etc.

In one aspect, the invention provides compound libraries wherein the compounds of such libraries can be subjected to enrichment for one or more desired activities on a continuously amplifying population.

In the methods of the present invention compounds having one or more desired activities are enriched to yield a subpopulation of nucleic acid sequences. The enriched subpopulation(s) of nucleic acid sequences serve as the starting material for repeating the step-wise synthesis of additional compounds.

Alternatively, the enriched subpopulation of nucleic acid sequences is amplified by non-specific polymerase chain reaction (PCR), and a new chemical reaction site added prior to repeating the step-wise synthesis of additional compounds.

A process termed "polynucleotide or gene shuffling" may also be applied to the present invention. In such a process, the enriched subpopulation of nucleic acid sequences is treated with one or more restriction enzymes under conditions effective to produce a partial digest by cleavage at a sequence-specific restriction enzyme site within each spacer sequence. The partially digested nucleic acid sequences are rejoined and a new chemical reaction site added prior to repeating the step-wise synthesis of additional compounds.

Compound libraries which are synthesized under the direction of compound-specific synthesis-directing nucleic acid tags are also provided by the present invention. In this aspect, the nucleic acid sequences which direct the synthesis of the compounds can be subjected to genetic recombination or in vitro evolution by repeated cycles of enrichment and step-wise synthesis; enrichment, PCR amplification and step-wise synthesis; or enrichment, partial digestion, rejoining of fragments and stepwise synthesis to yield a highly enriched subpopulation of synthesis-directing nucleic acid sequences.

Preferably, subpopulations of enriched compounds are produced by the methods of the present invention by selecting for activities which include, but are not limited to, modulation of enzymatic activity, modulation of non-enzymatic catalytic activity, modulation of protein-protein interactions and modulation of receptor/ligand interactions, etc.

The invention also provides a method for library splitting on the basis of sequence hybridization post-synthesis. In this aspect, a complete library is synthesized, split by hybridization based on the different sequence directing nucleic acid tag attached to each library member and further step performed on the split library.

Preferred types of compounds in the compound libraries of the present invention include, but are not limited to, small molecules with different chemical sequences, catalysts useful for the synthesis of complex molecules from simple substrates, inorganic compounds with useful properties as materials, non-ribosomally produced polypeptides, peptoids, polyketide-based natural products or subunit oligomers, e.g., polypeptides, polynucleotides etc.

Further, the invention provides a method to perform all genetic manipulations possible with natural biopolymers (through the manipulation of DNA instructions) on such DNA-templated combinatorial libraries of compounds as a means to provide a method to identify useful compounds from large combinatorial libraries of compounds, as described above.

These and other objects and features of the invention will become more fully apparent when the following detailed description of the invention is read in conjunction with the accompanying drawings.

DETAILED DESCRIPTION OF THE INVENTION

I. Definitions

Figure 1:
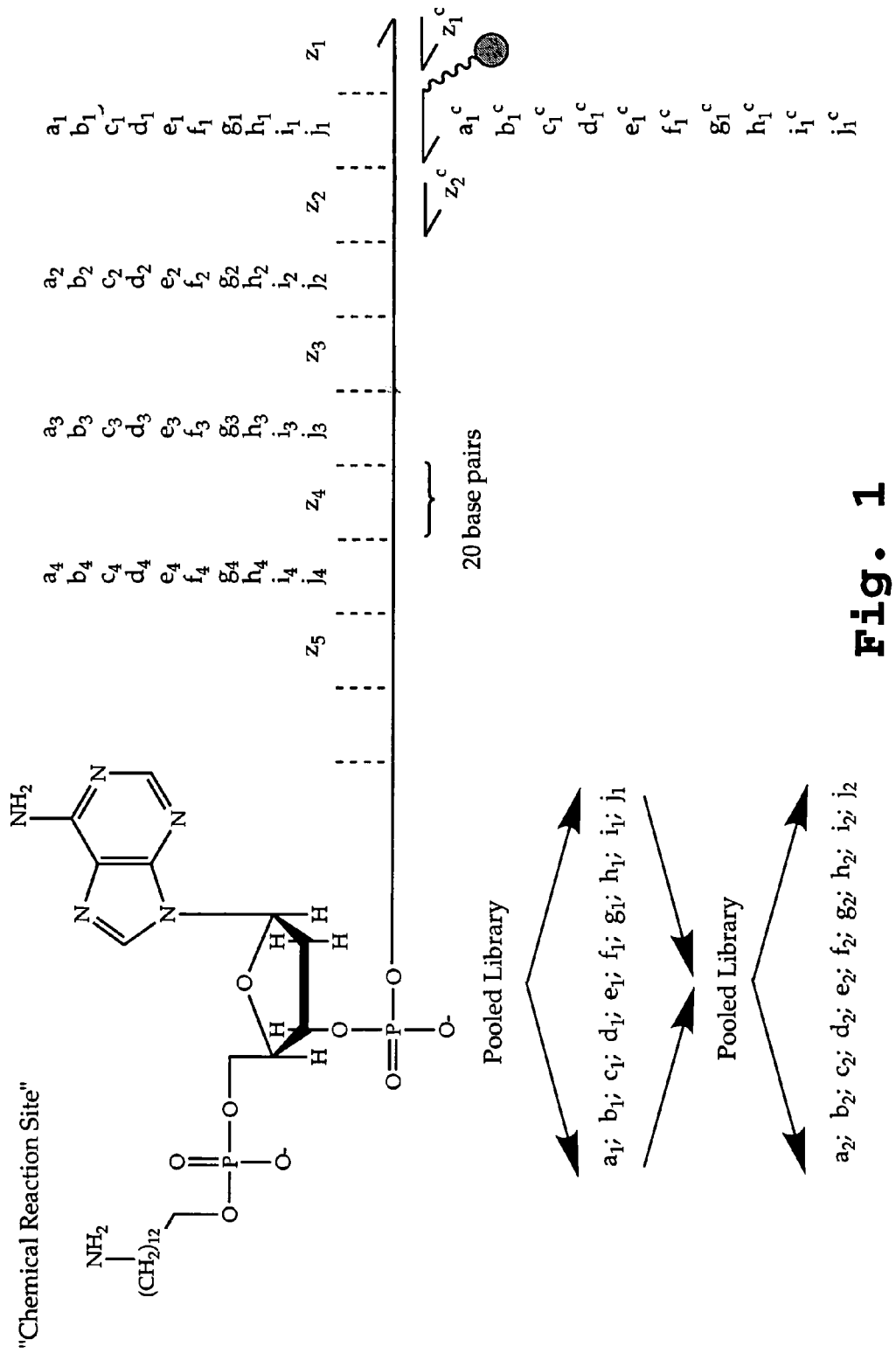
FIG. 1. depicts an exemplary DNA-directed splitting of a library of fragments. The degenerate family of DNA fragments consists of catenated 20 base-pair nucleotide sequences, which are either constant ($z_1$-$z_5$) or variable ($a_1$-$j_4$). The letters $a_1$ through $j_4$ in the variable regions of the DNA fragments denote distinct 20 nucleotide sequences with orthogonal hybridization properties. To carry out the first split, the degenerate family of fragments are passed over a set of ten different affinity resins displaying the sequences $a_1^c$-$j_1^c$, which are complementary to the sequences $a_1$-$j_1$ in the first variable region (one affinity resin is represented by the shaded ball). Ten sub-pools of the original family of fragments result. Each sub-pool is coupled to a distinct chemical monomer at the chemical reaction site. The sub-pools are recombined, and the library is split into a new set of sub-pools based on the sequences $a_2$-$j_2$, etc.
Figure 2:
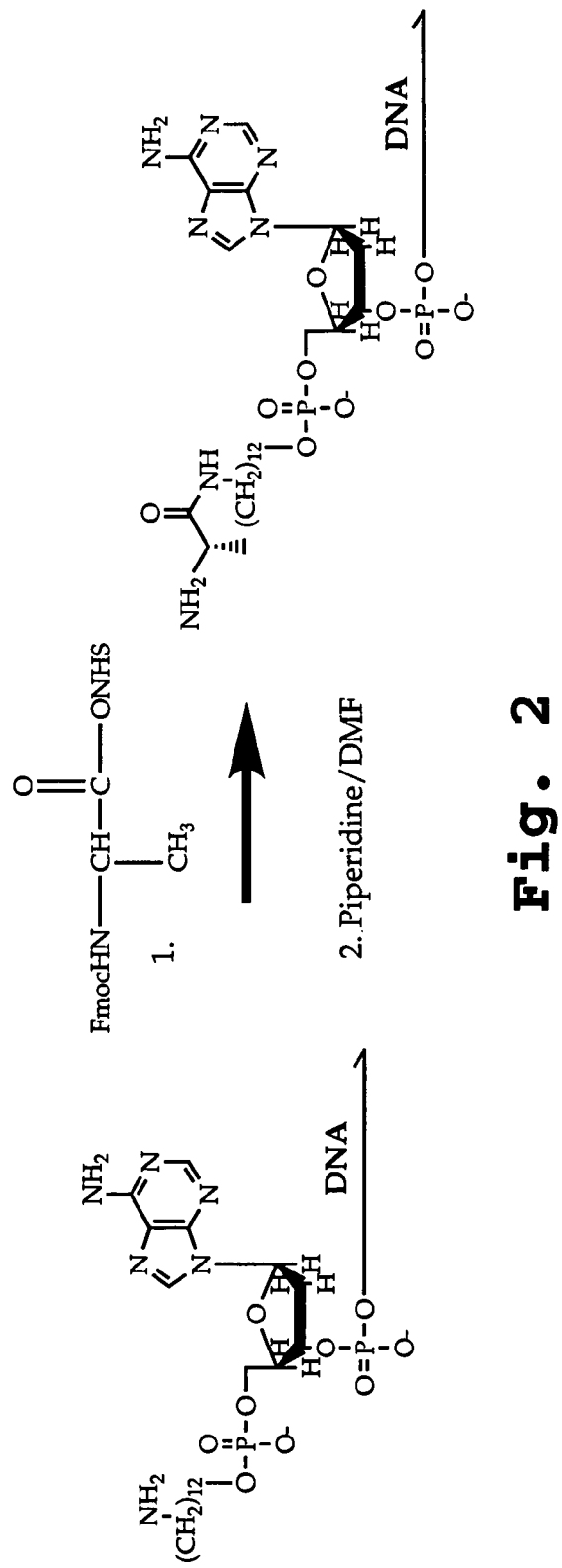
FIG. 2. depicts an example of chemical coupling at the chemical reaction site. A DNA fragment absorbed onto DEAE-Sepharose resin is treated with the NHS ester of FMOC-Alanine in DMF. The FMOC protecting group is removed with piperidine to provide the DNA fragment coupled to the amino acid alanine. The process can be repeated many times, and with a variety of amino acids, to produce polypeptide libraries.

The term "combinatorial library" is defined herein to mean a library of molecules containing a large number, typically between $10^3$ and $10^6$ different compounds typically characterized by different sequences of subunits, or a combination of different sequences of side chains and linkages.

The term "combinatorial library of subunit oligomers" is defined herein to mean a set of oligomers containing substantially each sequence permutation that can be formed by placing a selected one of a number of different subunits at each of a selected number of residue positions. "Different-sequence oligomer compounds" are oligomers, such as oligonucleotides, oligonucleotide analogs, oligopeptides, oligopeptide analogs, oligosaccharides, or lipopeptides with different permutations of lipid and/or sequences in the peptide moieties, glycopeptides with different sequence permutations in the saccharide and/or peptide moieties, non-biological oligomers with different-sequence permutations, or different-substituent compounds in a small-molecule library.

The terms "base-specific duplex formation" or "specific hybridization" refer to temperature, ionic strength and/or solvent conditions effective to produce sequence-specific pairing between a single-stranded oligonucleotide and its complementary-sequence nucleic acid strand, for a given length oligonucleotide. Such conditions are preferably stringent enough to prevent or largely prevent hybridization of two nearly-complementary strands that have one or more internal base mismatches. Preferably the region of identity between two sequences forming a base-specific duplex is greater than about 5 bp, more preferably the region of identity is greater than 10 bp.

The terms "polymerase chain reaction" and "PCR" refer to a process of amplifying one or more specific nucleic acid sequences, wherein (i) oligonucleotide primers which determine the ends of the sequences to be amplified are annealed to single-stranded nucleic acids in a test sample, (ii) a nucleic acid polymerase extends the 3' ends of the annealed primers to create a nucleic acid strand complementary in sequence to the nucleic acid to which the primers were annealed, (iii) the resulting double-stranded nucleic acid is denatured to yield two single-stranded nucleic acids, and (iv) the processes of primer annealing, primer extension, and product denaturation are repeated enough times to generate easily identified and measured amounts of the sequences defined by the primers. The sequential annealing, extension and denaturation steps are controlled by varying the temperature of the reaction container, normally in a repeating cyclical manner. Annealing and extension are typically carried out between 40-80° C., whereas denaturation requires temperatures between about 80 and 100° C. A "thermal cycler", such as Perkin Elmer Model 9600, is typically used to regulate the reactions.

The terms "oligonucleotides" or "oligos" as used herein refer to nucleic acid oligomers containing between about 3 and up to about 50, and typically from about 5 to about 15 nucleic acid subunits. In the context of oligos which direct the synthesis of the library compounds of the present invention, the oligos may include or be composed primarily of nucleotide analog subunits, or other subunits capable of forming sequence-specific Watson-Crick base pairing, when assembled in a linear polymer, with the proviso that the free ends of the oligos are ribonucleotide or deoxyribonucleotide subunits capable of providing a suitable substrate for strand-directed polymerization in the presence of a DNA polymerase and one or more nucleotide triphosphates, e.g., conventional deoxyribonucleotides with free 3' OH groups. A "known-sequence oligo" is an oligo whose nucleic acid sequence is known.

The term "oligonucleotide analog" is defined herein to mean a nucleic acid that has been modified and which is capable of some or all of the chemical or biological activities of the oligonucleotide from which it was derived. An oligonucleotide analog will generally contain phosphodiester bonds, although in some cases, oligonucleotide analogs are included that may have alternate backbones. (See, E. G., several nucleic acid analogs described in Rawls, C & E News, Jun. 2, 1997, page 35). Modifications of the ribose-phosphate backbone may facilitate the addition of additional moieties such as labels, or may be done to increase the stability and half-life of such molecules. In addition, mixtures of naturally occurring nucleic acids and analogs can be made. Alternatively, mixtures of different nucleic acid analogs, and mixtures of naturally occurring nucleic acids and analogs may be made. The oligonucleotides may be single stranded or double stranded, as specified, or contain portions of both double stranded or single stranded sequence. The oligonucleotide may be DNA, RNA or a hybrid, where the nucleic acid contains any combination of deoxyribo-and ribo-nucleotides, and any combination of bases, including uracil, adenine, thymine, cytosine, guanine, inosine, xathanine hypoxathanine, isocytosine, isoguanine, etc.

The "subunit oligomers" produced by the methods of the present invention typically have 3 to 20 residue positions at which the subunit assumes one of a plurality of possible forms, e.g., different nucleic acid or amino acid side chains.

"Different-sequence small-molecule compounds" are small organic molecules, typically, but not necessarily, having a common parent structure, such as a ring structure, and a plurality of different R group substituents or ring-structure modifications, each of which takes a variety of forms, e.g., different R groups. Such compounds are usually non-oligomeric (that is, do not consist of sequences of repeating similar subunits) and may be similar in terms of basic structure and functional groups, but vary in such aspects as chain length, ring size or number, or patterns of substitution.

The term "chemical reaction site" as used herein refers to a chemical component capable of forming a variety of chemical bonds including, but not limited to; amide, ester, urea, urethane, carbon-carbonyl bonds, carbon-nitrogen bonds, carbon-carbon single bonds, olefin bonds, thioether bonds, and disulfide bonds.

The terms "nucleic acid tag" and "nucleic acid support" are defined herein to mean the nucleic acid sequences which comprise a plurality of different first hybridization sequences, a mixture of different second hybridization sequences, and a chemical reaction site. Such "nucleic acid tags" are capable of directing the synthesis of the combinatorial library of the present invention and are also termed "synthesis-directing nucleic acid tags".

The term "tag-directed synthesis" refers to the fact that the plurality of compounds synthesized by the methods of the present invention is directed by the nucleic acid tag.

The term "continuously amplifying population" refers to the continuously increasing plurality of compounds produced by the iterative methods of the present invention.

The term "genetic recombination" refers to enrichment of the plurality of compounds produced by the methods of the present invention for those compounds having one or more desired activities by performing the steps of enrichment, partial digestion, rejoining the partially digested sequences and further stepwise synthesis to yield a highly enriched subpopulation of nucleic acid sequences which are bound to compounds having one or more desired activities.

In another aspect, the invention provides combinatorial compound libraries which can be subjected to genetic recombination or in vitro evolution by repeated cycles of enrichment and step-wise synthesis, enrichment, PCR amplification and step-wise synthesis or enrichment, partial digestion, reformation and stepwise synthesis to yield a highly enriched subpopulation of nucleic acids which are bound to compounds having one or more desired activities.

The term "selection for a desired activity" means evaluating one or more of the plurality of compounds produced by the methods of the invention for the ability to modulate a chemical or biological reaction.

The term "receptor" refers to a molecule that has an affinity for a given ligand which can be naturally occurring or synthetic molecule. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

The term "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

The term "modulate" as used herein refers to a change in a particular biological activity. Modulation may relate to an increase or a decrease in biological activity, binding characteristics, or any other biological, functional, or immunological property of the molecule.

The term "agonist" as used herein, refers to a molecule which is capable of modulating a biological activity of, e.g., a receptor by inducing, increasing, or prolonging the duration of the biological activity mediated by the receptor. Agonists may themselves be polypeptides, nucleic acids, carbohydrates, lipids, or derivatives thereof, or any other molecules which bind to and modulate the activity of the receptor.

The term "antagonist" as used herein, refers to a molecule which, when bound to, e.g., a receptor modulates the activity of the receptor by blocking, decreasing, or shortening the duration of the biological activity mediated by the receptor. Antagonists may themselves be polypeptides, nucleic acids, carbohydrates, lipids, or derivatives thereof, or any other molecules which bind to and modulate the activity of the receptor.

Other terms used herein should be construed to take on meanings customary in the art, unless otherwise defined herein.

II. Strategy for Synthesis of Combinatorial Libraries

The present invention provides encoded combinatorial chemical libraries which comprise a plurality of species of bifunctional molecules that each define a different chemical structure and that each contain a unique identifier nucleic acid sequence whose sequence defines, and directs the synthesis of the corresponding chemical structure.

The invention is based on the traditional split-and-recombine strategy for synthesis of combinatorial libraries comprising two or more synthetic steps. In a related approach, a traditional split-and-recombine strategy for synthesis of combinatorial libraries has been described. [Chen et al. (1996); Ellman and Gallop, (1998)]. For example, in a combinatorial synthesis consisting of i steps, for which j different chemical coupling reactions are performed at each step, $j^i$ compounds will be present in the final library. The traditional split and-recombine strategy is carried out using the following steps; (i) at the beginning of each of the i steps, the pool of solid tags is randomly split into j subsets, (ii) each of the j subsets of solid tags is subjected to a different chemical coupling step, and (iii) after the chemical coupling step, the subsets are recombined into a single pool. This recombined pool is again randomly divided into j subsets (specifically as in (i) above) at the beginning of the next step in the library synthesis. In the synthesis of peptide libraries, for example, the coupling step is the addition of an amino-acid active ester to a free amine group on the solid tag. Each of the j subsets is coupled to a different amino acid (e.g. alanine coupled to subset #1, arginine to subset #2, cysteine to subset #3 etc.). For example, a split-and-recombine synthesis of 10 synthetic steps, with 10 coupling reactions at each step, would yield a final library size of $10^{10}$.

The methods for synthesizing and screening combinatorial libraries as described herein are not restricted to DNA, RNA and polypeptides, as are the biological selection methods such as "phage display" [Abelson, J. N., *Methods in Enymology* 267: 1-483 (1996)] and methods for selection of reactive DNA and RNA molecules for large DNA libraries that are amplified iteratively by PCR [SELEX, Fitzwater and Polisky, *Methods Enzymol* 267:275-301 (1996)], which have been previously described.

The invention further provides a library of nucleic acid tags, also termed nucleic acid supports for use in directing the synthesis of a plurality of compounds wherein each tag has a first segment having a selected one of a plurality of different first hybridization sequences, a mixture of different second hybridization sequences, and a chemical reaction site; and a second segment having a selected one of a plurality of different second hybridization sequences and a mixture of different first hybridization sequences.

The methods of the present invention provide subsets of nucleic acid tags generated by base-specific duplex formation between each different first hybridization sequence and a complementary oligonucleotide or oligonucleotide analog. The chemical reaction sites in each of the subsets are reacted with a selected reagent to form a reagent-specific compound intermediate.

In one preferred embodiment, the nucleic acid tag comprises a first hybridization sequence, a second hybridization sequence and a chemical reaction site.

In a preferred aspect, a complementary oligonucleotide or oligonucleotide analog useful in the methods of the present invention is bound to one of a plurality of surface bound reagents.

The methods of the present invention provide that the steps of formation of subsets of nucleic acid sequences by base-specific duplex formation be repeated and a chemical subunit added to the chemical reaction site or last added chemical subunit within each subset until synthesis of the plurality of compounds is complete.

In general, the synthesis of a plurality of compounds requires two or more synthetic steps. In a preferred aspect, each subset of nucleic acid sequences includes at least 5 separate hybridization sequences. In a more preferred aspect each subset of nucleic acid sequences includes at least 10 separate hybridization sequences. In some cases, each subset of nucleic acid sequences includes more than 10 separate hybridization sequences.

A. An Exemplary Encoding Scheme

The genetic encoding scheme described below represents one of many different possible embodiments of the encoding schemes encompassed by the present invention. All of the possible encoding schemes that are encompassed under this invention are based on differential hybridization to nucleic acid tags during a split-and-recombine synthesis.

1. Nucleic Acid Tags.

In the present invention, the conventional solid support (typically a polystyrene/polymethylacrylate bead, or a polyethyleneglycol hybrid thereof) has been replaced with a nucleic acid sequence.

In an exemplary embodiment the nucleic acid tag is DNA and contains at least 220 base-pairs and more preferably contains 420 base pairs. In some cases the nucleic acid tag contains more than 420 base pairs.

In one exemplary embodiment, the nucleic acid tag consists of 21 regions of twenty base pairs. Eleven of these regions are denoted $C_1 \rightarrow C_{11}$, wherein, C is an abbreviation for "constant" and refers to the "spacer" sequences described above. In this embodiment, the ten remaining regions are denoted $V_1 \rightarrow V_{10}$ wherein, V is an abbreviation for "variable" and refers to the hybridization sequences which are different for each group of subsets of nucleic acid sequences. In this embodiment, every V region is bordered by two different C regions.

The pool of nucleic acid tags is degenerate, meaning that almost all of the nucleic acid tags differ from one another in nucleotide sequence. The nucleotide differences between different nucleic acid tags reside entirely in the hybridization sequences. For example, in one embodiment in the $V_1$ region, ten different twenty base-pair sequences are present. Each unique twenty base-pair sequence may be referred to as a "ZIP code". Thus ten different "ZIP codes", denoted $a_1$, $b_1$, $c_1 \ldots j_1$, appear in the $V_1$ region of the different nucleic acid tags. Likewise, ten more unique "ZIP codes", denoted $a_2$, $b_2$, $c_2 \ldots j_2$, appear in the $V_2$ region of the different nucleic acid tags. A third set of 10 unique ZIP codes appears in the $V_3$ region, etc.

In this embodiment, all of the DNA tags share the same twenty base-pair sequence in designated spacer regions, i.e., the $c_1$ spacer region is denoted $z_1$. A different 20 base-pair sequence, z2, appears in the $C_2$ region of every DNA tag. Accordingly in an embodiment where the nucleic acid tag contains 420 base pairs, in regions $C_3 \rightarrow C_{11}$, all of the tags have the spacer sequences $Z_3 \rightarrow Z_{11}$, respectively.

Thus each 420 base pair nucleic acid tag consists of an ordered assembly composed of 111 different twenty base-pair building blocks, the 100 ZIP codes ($a_1$, $b_1$, $c_1 \ldots d_5$, $e_5$, $f_5, \ldots h_{10}$, $i_{10}$, $j_{10}$) and the 11 spacer regions ($z_1 \ldots z_{11}$). The 111 twenty base-pair building blocks have the following properties: (i) micromolar concentrations of all 111 sequences hybridize to their complementary DNA sequences efficiently in solution at a specified temperature designated Tm, and (ii) the 111 sequences are orthogonal to each other with respect to hybridization, meaning that none of the 111 sequences cross-hybridizes efficiently with another of the 111 sequences, or with the complement to any of the other 111 sequences, at the temperature Tm.

The degenerate nucleic acid tags are assembled from their constituent building blocks by the primerless PCR assembly method described by Stemmer et al., Gene 164(1):49-53 (1995).

2. The Chemical Reaction Site

The 5' alcohol of the 5' base of the nucleic acid tag is modified with a commercially available reagent which introduces a phosphate group tethered to a linear spacer, e.g., a 12-carbon and terminated with a primary amine group (e.g., Glen Research catalog #10-1912-xx or numerous other reagents which are available for introducing thiols or other chemical reaction sites into synthetic DNA).

The primary amine represents the chemical reaction site on which the compound library is synthesized. Many different types of chemical reaction sites (in addition to primary amines) can be introduced at the 5' terminus of the nucleic acid tag. Exemplary chemical reaction sites include, but are not limited to, chemical components capable of forming amide, ester, urea, urethane, carbon-carbonyl bonds, carbon-nitrogen bonds, carbon-carbon single bonds, olefin bonds, thioether bonds, and disulfide bonds. In the case of enzymatic synthesis, co-factors may be supplied as are required for effective catalysis. Such co-factors are known to those of skill in the art. An exemplary cofactor is the phosphopantetheinyl group useful for polyketide synthesis.

B. Carrying Out a DNA-Templated Split

The compound library may be split into subsets at each step of the split-and-recombine combinatorial synthesis by differential hybridization of the nucleic acid tag to complementary oligonucleotides or oligonucleotide analogs bound to a solid support, e.g., polystyrene beads.

In a preferred embodiment, the hybridization sequence of each nucleic acid tag comprises at least 10 nucleotides.

The reagents described below are used to carry out the first step of an exemplary encoded split and are analogous to those used to carry out subsequent splits.

Oligonucleotides or oligonucleotide analogs which represent the complementary sequences to each of the hybridization sequences of the nucleic acid tags are synthesized. The 5' alcohols of the 5' bases of the each oligonucleotide or oligonucleotide analog are modified with a commercially available reagent which introduces a phosphate group tethered to a linear spacer, having for example six carbons and terminated with a thiol group (Glen Research catalog #10-1926-xx). Each of the thiol-bearing oligonucleotides or oligonucleotide analogs is immobilized through a thioether linkage to a macroporous resin (e.g., polystyrene, MPS; Biopore catalog #NH-2CM, L-970317) bearing electrophilic bromoacetamide groups (the preparation of which is described below). Thus a number of affinity resins result, each bearing a unique oligonucleotide or oligonucleotide analog. Each of the affinity resins is loaded into its own column with luer-lock fittings at either end and the columns connected in a linear sequence.

Numerous variants on the DNA encoding strategy, the attachment of chemical reaction sites to the DNA, and the specific chemistry or biochemistry used to construct the compound library are possible. Variation in the specific resins used to carry out the library splits, and to perform the chemical/biochemical coupling steps are also possible.

By way of application to the exemplary embodiment described above, the nucleic acid tag comprises 420 base pairs and 10 hybridization sequences. In this case, 10 different affinity resins and corresponding columns are used to form 10 subsets of nucleic acid sequences in each step of the synthesis of the compound library.

An exemplary first nucleic acid-encoded split is performed by contacting, i.e. pumping a high-salt aqueous solution containing the entire pool of different nucleic acid tags cyclically over the linear sequence of affinity columns under high stringency conditions [See, e.g., Southern, E M et al., *Nucl Acids Res.* 22(8) 1368-1373 (1994)], using a peristaltic pump for a time sufficient for all of the specific hybridization sequences of each DNA to hybridize to the oligonucleotide or oligonucleotide analogs bound to the columns. The DNA encoded split is completed simply by breaking the luer-lock linkages between the affinity columns. At this point the different DNA tags have been divided into physically separate subsets on the basis of the specific hybridization sequence in the V region of each tag.

To carry out the DNA-templated split for the second and subsequent synthetic steps, new affinity columns are prepared which display oligonucleotides corresponding to additional groups of different hybridization sequences bound to the polystyrene resin. These columns separate the DNA tags into additional subsets on the basis of which of possible nucleic acid sequences is present in the hybridization region of each nucleic acid tag. In a preferred embodiment at least 5 separate hybridization steps are preformed. In an even more preferred embodiment at least 10 separate hybridization steps are preformed.

The MPS resin described above is prepared from commercially available chloromethyl MPS resin in four steps (Biopore catalog #NH-2CM, L-970317): (i) the chloromethyl MPS resin is coupled to thioglycolic acid (ii) the N-hydroxy succinimide active ester of the coupled thioglycolic acid is prepared (iii) a Jeffamine 1500 molecular weight diamine (Fluke chemical #14535) is coupled to the resin by formation of an amide bond with the thioglycolic active ester (iv) the second amine of the coupled Jeffamine is acetylated with bromoacetic anhydride to produce the final bromoacetamide functionalized MPS resin.

Chemical Coupling

Each subset of nucleic acid tags formed by hybridization as described above is subjected to a different synthetic coupling reaction.

By way of example, a polypeptide may be formed by the methods of the present invention, as described below.

For synthesis of a polypeptide on the linker substrate in the direction of carboxy to amino terminus, a free amino terminus on the linker is required that can be conveniently blocked and deblocked as needed. A preferred amino terminus blocking group is a fluorenylmethoxycarbonyl group (FMOC).

For example, to couple an Fmoc-protected amino-acid to the to the primary amine "chemical reaction site" which is covalently attached to the synthesis-directing nucleic acid sequence or tag, the following steps are carried out: (i) the DNA tags hybridized to the affinity columns are transferred onto columns, e.g., hydroxyapatite resin columns (Bio-Rad Macro-Prep Ceramic Hyroxyapatite TYPE II catalog #1588200) with elution in 300 μM CaCl or DEAE Sepharose fas (Pharmacia 17-0709-01) with elution in 10 mM acetate at pH 5.0 with 0.005% triton). The DNA tags remain non-covalently bound to the hydroxyapatite or sepharose resin in numerous organic solvents (for example DMF, acetonitrile, ethanol, and mixtures of those solvents with water). Thus organic reagents can be flowed over the columns and reacted with the chemical reaction sites on the DNA tags in the same manner that conventional solid phase chemical synthesis is carried out. Accordingly, a different Fmoc-protected amino-acid preactivated with N[(1H-benzotriazol-1-yl) (dimethylamino) methylene]-N-methylmethanaminium tetrafluoroborate (TBTU) or as an N-hydroxy succinimide ester in DMF is flowed over each hydroxyapatite or sepharose column, resulting in the acylation of the primary amines of the DNA tags on each of the hydroxyapatite or sepharose columns with an Fmoc-protected amino acid [Albericio, F. and Carpino L A, *Methods in Enymology* 289:104-26 (1997)]. Following acylation, the Fmoc group is removed from the newly added amino acid by flowing a piperidine/DMF solution over the hydroxyapatite or sepharose columns, thus presenting a new primary amine ready for the next coupling step.

Numerous methods for modification of DNA are known to those of skill in the art and readily incorporated into the methods described herein [See, e.g., Chu, B C, et al. *Nucleic Acids Research* 11(18):6513-6529 (1983)]. By way of further example, nucleotides may be synthesized by various methods known to those of skill in the art. [See e.g., "Oligonucleotide Synthesis: A Practical Approach", ed. M. J. Gait, JRL Press, New York, N.Y. (1990)].

An entire compound library is synthesized by carrying out alternate rounds of DNA-templated library splitting and chemical and/or biochemical coupling to each subsets of nucleic acid tags.

The plurality of chemical compounds produced by the methods of the present invention are linked to nucleic acid sequence tags which facilitate identification of the chemical structure.

Conventional DNA sequencing methods are readily available and useful for a determination of the sequence of the synthesis-directing nucleic acid tags. See, e.g., Maniatis et al., eds, "Molecular Cloning: A Laboratory Manual", Second Edition, Cold Spring Harbor, N.Y. (1989).

III. Selection, Amplification and Enrichment

The compound library may be screened for a desired activity, for example the ability to catalyze a particular reaction or to bind with high affinity to an immobilized receptor. In most cases, the subpopulation of molecules with the desired activity, as well as their nucleic acid tags, are physically partitioned away from siblings during the selection. Following selection, the nucleic acid tags attached to the selected molecules are amplified by the polymerase chain reaction [PCR] [Saiki et al, *Science* 239(4839) 487-491 (1988)]. The 5'hydroxyl of the 5'-end primer used to PCR amplify the coding strand is modified with a phosphate group tethered to a fresh primary amine chemical reaction site. After amplification, the coding strand is separated from the non-coding strand. Because the nucleic acid tags direct the library synthesis in the present invention, rather than merely reporting on the synthetic history of individual compounds, the coding strands amplified from the first library can be used to direct the construction of a second generation compound library. Iteration of this procedure, by carrying out multiple rounds of selection, DNA tag amplification, and library resynthesis, allows individual desirable compounds to "evolve" from extremely complex libraries.

A. Screening Library for a Desired Activity

An entire compound library or individual library members produced by the methods of the present invention may be evaluated for one or more desired activities in screening assays capable of distinguishing compounds which modulate an activity or possess a desired structural or functional property.

Exemplary assays and functional analyses include, but are not limited to, enzymatic assays, non-enzymatic catalytic assays, protein-protein binding assays, receptor/ligand binding assays and cell-based assays. More specifically, exemplary cell-based methods provided by the present invention are based on; (1) differential binding of library compounds to a cell surface (i.e. binding to cancer cell and not a non-cancer cell), (2) binding of library compounds to components of a cell extract (e.g., binding to a cell fraction produced by separating an entire cell extract on a sucrose gradient), (3) library compounds capable of endocytosis by a cell, and (4) in vivo localization and binding properties of library compounds by injecting the library into an animal. [See, e.g., Arap, W., et al., *Science* 279(5349): 377-80. (1998) which describes in vivo selection of phage display libraries to isolate peptides that home specifically to tumor blood vessels]

As will be appreciated by those of skill in the art, such assays may be preformed on entire libraries of compounds synthesized by the methods described herein or sub populations derived therefrom.

The number of possible receptor molecules for which ligands may be synthesized and identified by the methods of the present invention is virtually unlimited. Exemplary receptor molecules include, but are not limited to antibodies, growth factors, hormones, enzyme substrates, interferons, interleukins, intracellular and intercellular messengers, lectins, cellular adhesion molecules, and the like. Additional exemplary ligands include, but are not limited to, carbohydrates, non-protein organic compounds, metals, peptide mimetics, non-ribosomally produced polypeptides, conotoxins and polyketides, etc.

Desired compounds produced by the nucleic acid tag-directed combinatorial library methods of the present invention include, but are not limited to, small organic molecules, polyketides, subunit oligomers and catalysts for the synthesis of complex molecules from simple substrates, e.g., transition metal mediated reactions termed "domino" reactions which are highly efficient processes that allow for production of large libraries of complex structures in relatively few steps beginning with simple precursors. [See, e.g., Tietze and Lieb, *Curr Opin Chem Biol* 2:63-371 (1998)]

B. In Vitro Evolution of Selected Compounds-Gene Shuffling

In addition to allowing amplification of selected library members, the present invention permits evolution of the encoded compound libraries. More specifically, genetic recombination between the nucleic acid tags which encode selected subpopulations of compounds is carried out in vitro by mutagenesis or random fragmentation of the nucleic acid tag sequence, followed by the generation of related nucleic acid sequences ["gene shuffling", Stemmer, *Nature,* 370:389-391 (1994); U.S. Pat. No. 5,811,238 (1998)], and subsequent step-wise synthesis of additional compounds.

In one embodiment of the invention, a unique restriction site is introduced into each specific hybridization sequence. By way of example, partial digestion of a library with 11 specific hybridization sequences is accomplished by partial digestion with 11 corresponding restriction enzymes, followed by a primerless PCR reassembly reaction, allowing the nucleic acid tags for compounds that have been selected out of the library to be recombined with one another and further synthetic steps carried out. By analogy to gene shuffling for protein synthesis [Crameri, et al., *Nature* 391(6664):288-291 (1998)], the ability to carry out genetic recombination of compound libraries vastly increases the efficiency with which the diversity in the compound libraries can be explored and optimized.

Accordingly, the invention provides for polynucleotide shuffling to yield a population of variant nucleic acid sequences, capable of directing the synthesis of structurally-related, and/or functionally-related molecules, and/or variants thereof to create compounds having one or more desired activities. For example, molecules capable of binding to the 5' untranslated region (UTR) of mRNA may be identified in this manner.

It is also contemplated that the method of this invention can be used for the in vitro amplification of a selected subpopulations of synthesis directing nucleic acid tags by PCR, either prior to or following "gene shuffling".

IV. Utility

The principle advantage of the current invention over previous methods for constructing and screening combinatorial compound libraries is that the tag directs and encodes the synthesis of the compound to which it is covalently attached (not merely reporting on the synthetic history of individual compounds), the tag can be used to create library subpopulations based on hybridization, the types of compounds that are synthesized are not limited to polypeptides and polynucleotides, the number of compounds that may be produced far exceeds that of traditional combinatorial libraries and the tag is a DNA molecule which can be amplified biochemically and improved by genetic recombination, and in vitro evolution.

While the invention has been described with reference to specific methods and embodiments, it will be appreciated that various modifications and changes may be made without departing from the invention. All patent and literature references cited herein are hereby incorporated by reference in their entireties.

The invention claimed is:

1. A method of tag-directed synthesis of a plurality of compounds wherein a nucleic acid tag directs and encodes the synthesis of a compound to which it is covalently attached, comprising:
   (a) providing a pool of subsets of nucleic acid tags, wherein each nucleic acid tag comprises a single stranded DNA sequence having a 5' terminus and a first variable hybridization sequence linked to a second variable hybridization sequence, wherein said 5' terminus is covalently attached to a chemical reaction site, and wherein each of said first and second variable hybridization sequences is different for each subset of nucleic acid tags;
   (b) splitting the pool of nucleic acid tags of step (a) to form a first group of subsets of nucleic acid tags for participating in a first synthetic reaction, by contacting said nucleic acid tags with a plurality of first immobilized nucleotide sequences, each designed to capture a subset of said nucleic acid tags by specific hybridization between one of said first variable hybridization sequences and one of said first immobilized sequences, and physically separating the subsets of said pool of nucleic acid tags on the basis of said first variable hybridization sequence of each nucleic acid tag and removing said first immobilized sequence;
   (c) carrying out the first synthetic reaction by reacting the chemical reaction sites of the nucleic acid tags in each of the subsets formed in step (b) with a selected one of a plurality of first reagents that couples a different chemical subunit to the chemical reaction site of each subset of nucleic acid tags under conditions effective to form a reagent-specific compound intermediate to produce a first group of subsets of reacted nucleic acid tags;
   (d) pooling the first group of subsets of reacted nucleic acid tags of step (c) to form a first pool of reacted nucleic acid tags;
   (e) splitting the first pool of reacted nucleic acid tags of step (d) to form a second group of subsets of reacted nucleic acid tags for participation in a second synthetic reaction, by contacting said first pool of reacted nucleic acid tags with a plurality of second immobilized nucleotide sequences, each designed to capture a subset of said first pool of reacted nucleic acid tags by specific hybridization between one of said second variable hybridization sequences and the second immobilized sequence, and physically separating the subsets of said first pool of reacted nucleic acid tags on the basis of said second variable hybridization sequence of each nucleic acid tag and removing said second immobilized sequence; and
   (f) carrying out the second synthetic reaction by reacting the reagent-specific compound intermediate of the reacted nucleic acid tag in each of the subsets formed in step (e) with a selected one of a plurality of second reagents that couples a different chemical subunit to the reagent-specific compound intermediate of each subset of reacted nucleic acid tags formed in step (e) under conditions effective to form a different sequence oligomer or different sequence small-molecule compound attached to a nucleic acid tag to produce a second group of subsets of reacted nucleic acid tags, whereby a plurality of compounds is produced.

2. The method of claim 1, wherein the plurality of first and second reagents in steps (c) and (f) include different oligomer subunits.

3. The method of claim 1, wherein the plurality of first and second reagents in steps (c) and (f) include different small molecule compound substituents.

4. The method of claim 1 for making a plurality of compounds requiring more than 2 synthetic steps wherein the second group of subsets of reacted nucleic acid tags produced in step (f) is subjected to one or more additional rounds of (i) pooling to form an Nth pool of reacted nucleic acid tags, (ii) splitting to form an Nth group of subsets of reacted nucleic acid tags, and (iii) synthesis to produce subsets of Nth reacted nucleic acid tags, and wherein each round includes an additional step-specific subset of Nth variable hybridization sequences and Nth immobilized nucleotide sequences for each synthetic step N greater than 2 and which further comprises, for each additional synthetic step N;
   (g) forming an Nth pool of reacted nucleic acid tags, wherein each of said nucleic acid tags of step (a) comprises said Nth variable hybridization sequence linked to said second variable hybridization sequence, and wherein each of said first, second and Nth variable hybridization sequences is different for each subset of nucleic acid tags;
   (h) splitting the Nth pool of reacted nucleic acid tags of step (g) to form an Nth group of subsets of reacted nucleic acid tags for participating in an Nth reaction step, by contacting said Nth pool of reacted nucleic acid tags with a plurality of said Nth immobilized nucleotide sequences, each designed to capture a subset of said reacted nucleic acid tags by specific hybridization between one of said Nth variable hybridization sequences and the Nth immobilized sequence, and physically separating the subsets of said Nth pool on the basis of said Nth variable hybridization sequence of each reacted nucleic acid tag and removing said Nth immobilized sequence;
   (i) carrying out the Nth reaction step by reacting the reacted nucleic acid tags in each of the subsets formed in step (h) with a selected one of a plurality of Nth-reaction reagents that couples a different chemical subunit to the different sequence oligomer or different sequence small-molecule compound of each subset formed in step (h) under conditions effective to produce subsets of Nth reacted nucleic acid tags; and
   (j) repeating steps (g)-(i) if necessary, until synthesis of the compounds is complete.

5. The method of claim 4 wherein each subset of nucleic acid tags includes at least 5 separate variable hybridization sequences.

6. The method of claim 1, wherein said nucleic acid tags within each subset further comprises for each subset of variable hybridization sequences, an adjacent constant spacer sequence separating that variable hybridization sequence from an adjacent one, each of said constant spacer sequences being the same for all subsets of nucleic acid tags and each variable hybridization sequence being different for each group of subsets of nucleic acid tags.

7. The method according to claim 1, for use in enriching the plurality of compounds for those having a desired compound activity, further comprising identifying from said plurality of compounds, one or more compounds having a desired activity to yield a subpopulation of nucleic acid tags, and using the subpopulation to carry out the method of claim 1.

8. The method according to claim 7, wherein said using the subpopulation includes:
   amplifying said subpopulation of nucleic acid tags by polymerase chain reaction (PCR), and
   adding a chemical reaction site.

9. The method of claim 6, wherein each of said constant spacer sequences comprises a unique restriction enzyme site, and wherein the method further comprises:

(g) identifying from said plurality of compounds, one or more compounds having a desired activity to yield a subpopulation of nucleic acid tags;

(h) amplifying said subpopulation of nucleic acid tags by polymerase chain reaction (PCR);

(i) treating said subpopulation of nucleic acid tags with one or more restriction enzymes under conditions effective to produce a partial digest;

(j) rejoining said partially digested nucleic acid tags; and (k) adding a new chemical reaction site to said partially digested nucleic acid tags and using the subpopulation to carry out the method of claim 1.

10. The method of claim 1, wherein each of said first and second immobilized nucleotide sequences are each bound to the surface of a solid phase reagent.

11. The method of claim 1, wherein said steps (c) and (f) include first transferring the subsets of said nucleic acid tags from said immobilized sequences to a solid support prior to said reacting.

12. The method of claim 1, wherein said chemical reaction site is covalently attached to said 5' terminus through a linker.

13. The method of claim 1, wherein said chemical reaction site is a chemical component capable of forming a chemical bond selected from amide, ester, urea, urethane, carbon-carbonyl bonds, carbon-nitrogen bonds, carbon-carbon single bonds, olefin bonds, thioether bonds, and disulfide.

14. The method of claim 1, wherein said chemical subunits are amino acids.

15. The method of claim 14, wherein said chemical reaction site is a primary amine, said amino acids are Fmoc-protected amino acids, said reacting couples a selected Fmoc-protected amino acid to said primary amine to form an amide bond, and said reacting is followed by removal of the Fmoc protecting group of said selected Fmoc-amino acid prior to a next reacting step.

16. The method of claim 15, wherein said reagent-specific compound intermediate is an amino acid presenting a new primary amine ready for a next reacting step.

17. The method of claim 6, wherein said variable hybridization sequences and said constant spacer sequences are catenated nucleotide sequences each at least 10 nucleotides long, and wherein said nucleic acid tag includes at least 5 variable hybridization sequences.

18. A method for the iterative synthesis and screening of a plurality of compounds to produce a subpopulation of compounds having a desired activity, wherein a nucleic acid tag directs and encodes the synthesis of the compound to which it is covalently attached, said method comprising:

(a) providing a pool of subsets of the nucleic acid tags in which each nucleic acid tag comprises a single stranded DNA sequence having a 5' terminus and a first variable hybridization sequence linked to a second variable hybridization sequence, wherein said 5' terminus is covalently attached to a chemical reaction site, and wherein each of said first and second variable hybridization sequences is different for each subset of nucleic acid tags;

(b) splitting the pool of nucleic acid tags of step (a) to form a first group of subsets of nucleic acid tags for participating in a first synthetic reaction, by contacting said nucleic acid tags with a plurality of first immobilized nucleotide sequences, each designed to capture a subset of said nucleic acid tags by specific hybridization between one of said first variable hybridization sequences and one of said first immobilized sequences, and physically separating the subsets of said pool of nucleic acid tags on the basis of said first variable hybridization sequence of each nucleic acid tag and removing said first immobilized hybridization sequence;

(c) carrying out the first synthetic reaction by reacting the chemical reaction sites of the nucleic acid tags in each of the subsets formed in step (b) with a selected one of a plurality of first reagents that couples a different chemical subunit to the chemical reaction site of each subset of nucleic acid tags under conditions effective to form a reagent-specific compound intermediate to produce a first group of subsets of reacted nucleic acid tags;

(d) pooling the first group of subsets of reacted nucleic acid tags of step (c) to form a first pool of reacted nucleic acid tags;

(e) splitting the pool of the first group of reacted nucleic acid tags of step (d) to form a second group of subsets of reacted nucleic acid tags for participation in a second synthetic reaction, by contacting said first pool of reacted nucleic acid tags with a plurality of second immobilized nucleotide sequences, each designed to capture a subset of said first pool of reacted nucleic acid tags by specific hybridization between one of said second variable hybridization sequences and the second immobilized sequence, and physically separating the subsets of said first pool on the basis of said second variable hybridization sequence of each nucleic acid tag and removing said second immobilized sequence;

(f) carrying out the second synthetic reaction by reacting the reagent-specific compound intermediate of the reacted nucleic acid tag in each of the subsets formed in step (e) with a selected one of a plurality of second reagents that couples a different chemical subunit to the reagent-specific compound intermediate of each subset of reacted nucleic acid tags formed in step (e) under conditions effective to form a different sequence oligomer or different sequence small-molecule compound to produce a second group of subsets of reacted nucleic acid tags;

(g) subjecting the second group of subsets of reacted nucleic acid tags produced in step (f) to one or more additional rounds of (i) pooling to form an Nth pool of reacted nucleic acid tags, (ii) splitting to form and Nth group of subsets of reacted nucleic acid tags, and (iii) synthesis to produce subsets of Nth reacted nucleic acid tags, wherein each round includes an additional step-specific subset of Nth variable hybridization sequences and Nth immobilized nucleotide sequences, and wherein each additional round comprises:

(h) forming an Nth pool of reacted nucleic acid tags, wherein each of said nucleic acid tags of step (a) comprises said Nth variable hybridization sequence linked to said second variable hybridization sequence, wherein each of said first, second and Nth variable hybridization sequences is different for each subset of nucleic acid tags;

(i) splitting the Nth pool of reacted nucleic acid tags of step (h) to form an Nth group of subsets of reacted nucleic acid tags for participating in an Nth reaction step, by contacting said Nth pool of reacted nucleic acid tags with a plurality of said Nth immobilized nucleotide sequences, each designed to capture a subset of said reacted nucleic acid tags by specific hybridization between one of said Nth variable hybridization sequences and the Nth immobilized sequence, and physically separating the subsets of said Nth pool on the basis of said Nth variable hybridization sequence of each reacted nucleic acid tag and removing said Nth immobilized sequence;

(j) carrying out the Nth reaction step by reacting the reacted nucleic acid tags in each of the subsets formed in step (i) with a selected one of a plurality of Nth-reaction reagents that couples a different chemical subunit to the different sequence oligomer or different sequence small-molecule compound of each subset formed in step (i) under conditions effective to produce subsets of Nth reacted nucleic acid tags;

(k) repeating steps (h)-(j) if necessary, until synthesis of a plurality of compounds is complete;

(l) identifying from said plurality of compounds of step (k), one or more compounds having a desired activity to yield a subpopulation of nucleic acid tags; and (m) producing a pool of nucleic acid tags based on the subpopulation of nucleic acid tags from step (l) and repeating steps (a)-(l) if necessary, until synthesis of a plurality of compounds having the desired activity is complete.

19. The method of claim 18, wherein said chemical reaction site is covalently attached to said 5' terminus through a linker.

20. The method of claim 18, wherein said chemical reaction site is a chemical component capable of forming a chemical bond selected from amide, ester, urea, urethane, carbonyl bonds, carbon-nitrogen bonds, carbon-carbon single bonds, olefin bonds, thioether bonds, and disulfide.

21. The method of claim 18, wherein said chemical subunits are amino acids.

22. The method of claim 21, wherein said chemical reaction site is a primary amine, said amino acids are Fmoc-protected amino acids, said reacting couples a selected Fmoc-protected amino acid to said primary amine to form an amide bond, and said reacting is followed by removal of the Fmoc protecting group of said selected Fmoc-amino acid prior to a next reacting step.

23. The method of claim 22, wherein said reagent-specific compound intermediate is an amino acid presenting a new primary amine ready for a next reacting step.

24. The method of claim 18, wherein said nucleic acid tags within each subset further comprises for each subset of variable hybridization sequences, an adjacent constant spacer sequence separating that variable hybridization sequence from an adjacent one, each of said constant spacer sequences being the same for all subsets of nucleic acid tags and each variable hybridization sequence being different for each group of subsets of nucleic acid tags.

25. The method of claim 24, wherein said variable hybridization sequences and said constant spacer sequences are catenated nucleotide sequences each at least 10 nucleotides long, and wherein said nucleic acid tag includes at least 5 variable hybridization sequences.

* * * * *